United States Patent
Parthasaradhi Reddy et al.

(10) Patent No.: US 8,354,541 B2
(45) Date of Patent: Jan. 15, 2013

(54) OPTICAL PURIFICATION OF ESOMEPRAZOLE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN)

(73) Assignee: Hetero Research Foundation (ID)

( * ) Notice: Subject to any disclaimer, the term of this patent is extended or adjusted under 35 U.S.C. 154(b) by 0 days.

(21) Appl. No.: 12/742,531

(22) PCT Filed: Nov. 18, 2008

(86) PCT No.: PCT/IN2008/000775
§ 371 (c)(1),
(2), (4) Date: May 12, 2010

(87) PCT Pub. No.: WO2010/058409
PCT Pub. Date: May 27, 2010

(65) Prior Publication Data
US 2011/0213155 A1    Sep. 1, 2011

(51) Int. Cl.
*C07D 401/12* (2006.01)
(52) U.S. Cl. .................................. 546/273.7
(58) Field of Classification Search ............... 546/273.7
See application file for complete search history.

(56) References Cited

U.S. PATENT DOCUMENTS

| 4,738,974 A | 4/1988 | Brandstrom |
| 5,714,504 A | 2/1998 | Lindberg et al. |
| 5,877,192 A | 3/1999 | Lindberg et al. |
| 2007/0259921 A1 | 11/2007 | Bolugoddu et al. |

FOREIGN PATENT DOCUMENTS

| CN | 1087739 A | 6/1994 |
| CN | 1223262 A | 7/1999 |
| DE | 4035455 A1 | 5/1992 |
| WO | 9427988 A1 | 12/1994 |
| WO | 9702261 A1 | 1/1997 |
| WO | 2004002982 A2 | 1/2004 |
| WO | 2005116011 A1 | 8/2005 |
| WO | 2005105786 A1 | 11/2005 |
| WO | 2006094904 A1 | 9/2006 |
| WO | 2007013743 A1 | 2/2007 |
| WO | 2007074099 A1 | 7/2007 |
| WO | 2008092939 A2 | 8/2008 |

OTHER PUBLICATIONS

Sigrist-Nelson, et al., Ro 18/5364, a potent new inhibitor of gastric (H+ + K+)-ATPase, Eur. J. Biochem, 1987, vol. 166, pp. 453-459.
International Search for PCT/IIN2008/000775 dated Nov. 18, 2008 and Written Opinion.

*Primary Examiner* — Patricia L Morris
(74) *Attorney, Agent, or Firm* — Ceasar, Rivise, Bernstein, Cohen & Pokotilow, Ltd.

(57) ABSTRACT

The present invention relates to process for optical purification of esomeprazole or a salt thereof. Thus, esomeprazole sodium having 20 to 1% R-omeprazole by weight of the sum of the contents of esomeprazole and R-omeprazole is precipitated from a solvent selected from an alcohol or a mixture of alcohols and the precipitated solid is collected to obtain optically pure esomeprazole sodium.

5 Claims, No Drawings

OPTICAL PURIFICATION OF ESOMEPRAZOLE

FIELD OF THE INVENTION

The present invention relates to process for optical purification of esomeprazole or a salt thereof.

BACKGROUND OF THE INVENTION

Omeprazole, chemically 5-methoxy-2-[[(4-methoxy-3,5-dimethyl-2-pyridinyl)methyl]sulfinyl]-1H-benzimidazole and its therapeutic uses were disclosed in European Patent No. 5129. Omeprazole is a well-known gastric acid secretion inhibitor, and is useful as an anti ulcer agent. Omeprazole has a stereogenic center at sulfur and therefore exist as two optical isomers such as R-omeprazole and S-omeprazole (esomeprazole).

The alkaline salts of (S)-enantiomer of omeprazole (esomeprazole), the pharmaceutical preparations of these salts and the method of treatment of gastric acid-related diseases using them were disclosed in U.S. Pat. Nos. 4,738,974, 5,877,192 and 5,714,504. The patents U.S. Pat. Nos. 4,738,974, 5,877,192 and 5,714,504 are incorporated herein by reference.

These compounds and structurally related compounds have a stereogenic center at sulfur and therefore exist as two optical isomers. The resolution processes of racemates of these compounds were for example disclosed in DE 4035455 and WO 94/27988. According to these processes chiral ether such as fenchyloxymethyl or chiral acyloxy methyl group such as mandeloyl—is introduced into the 1-position of benzimidazole ring of racemic sulfoxide compound to obtain a diastereomeric mixture, diastereomers are then separated and desired isomer is liberated from a separated diastereomer. The process requires either the preparation of fenchyloxymethyl chloride and then reaction with the racemic compound; or introduction of chloromethyl group on 1-position of benzimidazole ring, followed by reaction with the chiral auxiliary. We find that these intermediates are difficult to prepare and involve in many steps.

WO97/02261 disclosed a process for the optical purification of certain enantiomerically enriched benzimidazole derivatives by using a crystallization method.

Chinese Patent No. 1087739 disclosed a method of preparing esomeprazole by using (S)-(−)-binol (β-binapthol) as an optical resolution agent by inclusion of complex with (S)-(−)-binol Chinese Patent No. 1223262 was related to a process for the preparation of certain optically pure benzimidazole derivatives by inclusion complexation with binaphthyl phenol derivative.

The resolution of sulfoxide compounds including racemic omeprazole were described in WO 2004/002982. The method requires expensive reagents like titanium compounds, two chiral reagents namely diethyl-D-tartarate and L-Mandelic acid.

Enantioselective synthesis was described for example in Euro. J. Biochem. 166 (1987) 453 and U.S. Pat. No. 5,948,789. Disadvantages of these methods are that strict control of conditions is to be maintained and strict control of quantities of oxidizing agents is required for avoiding oxidation of desired sulfoxide to sulfone impurity. Moreover, these methods require expensive reagents like titanium isoproxide and diethyl-D-tartarate.

The process for the preparation of racemic benzimidazole sulfoxides such as omeprazole, useful as starting materials for preparing enantiomerically pure benzimidazole sulfoxides, from their corresponding sulfides involves a problem of over oxidation to form sulfone impurities.

WO2005/105786 and WO2005/116011 described the resolution methods for racemic benzimidazole sulfoxides.

WO2006/094904 disclosed a process for the resolution of 2-(2-pyridimylmethylsulfinyl)-benzimidazole derivatives by the inclusion complex with [1,1'-binapthalene]-2-2'-diol in presence of amine.

WO2007/013743 disclosed an improved optical resolution process for preparing optically pure esomeprazole and its salts by inclusion complex with (S)-(−)-binol.

WO2007/074099 disclosed process for the preparation of optically pure benzimidazole derivatives by inclusion complex with (S)-1,1,2-triphenyl-1,2-ethanediol.

WO2008/092939 disclosed a process for the preparation of substantially optically pure omeprazole with the formation of a complex by using chiral amine or chiral quaternary ammonium salt.

We have discovered a novel process for optical purification of esomeprazole. The object of the present invention is to provide an improved and commercially viable process for optical purification of esomeprazole or its salts.

DETAILED DESCRIPTION OF THE INVENTION

According to the present invention there is provided a process for optical purification of esomeprazole or a salt thereof, the said process comprises:
a. preparing a solution of esomeprazole sodium having 20 to 1% R-omeprazole by weight of the sum of the contents of esomeprazole and R-omeprazole in a solvent selected from an alcohol or a mixture of alcohols;
b. precipitating esomeprazole sodium; and
c. collecting the precipitated substantially pure esomeprazole sodium.

Substantially pure esomeprazole sodium obtained by the process of the present invention may optically be converted to esomeprazole free compound or any other salt of esomeprazole in substantially pure form.

It has been found that optical purification is not possible when esomeprazole having more than 80% R-omeprazole and optical purification occurs only when R-omeprazole content is in the range 20 to 1%.

The solution of esomeprazole sodium may be prepared (step-a) by the methods known such as by dissolving esomeprazole sodium in the solvent or by adding a source of sodium such as sodium hydroxide to a solution of esomeprazole in the solvent.

The precipitation of esomeprazole sodium in (step-b) may be carried out by the techniques known to the art such as aging, stirring, cooling, seeding, partial evaporation of the solvent etc. The esomeprazole is selectively precipitated leaving R-omeprazole in the solution.

The precipitated solid may be collected by, for example, filtration or centrifugation.

The solvent used in the process may preferably selected from methanol, ethanol and isopropyl alcohol, and more preferable being methanol.

The esomeprazole sodium used in step (a) may preferably have 20 to 3%, more preferably 15 to 5% of R-omeprazole by weight of the sum of the contents of esomeprazole and R-omeprazole.

Substantially pure esomeprazole sodium refers to esomeprazole sodium having higher chiral purity than the esomeprazole sodium used in step (a) of the present invention. The process can yield esomeprazole sodium having chiral purity higher than 99%. The process of the invention can be repeated until the desired chiral purity of esomeprazole sodium is obtained.

The following examples are given for the purpose of illustrating the present invention and should not be considered as limitations on the scope or spirit of the invention.

EXAMPLES

Preparative Example 1

Racemate of 5-Methoxy-2-[(3,5-dimethyl-4-methoxy-2-pyridyl)methylsulfinyl]-1H-benzimidazole (100 gm) was dissolved in dichloromethane (1000 ml) and dimethyl amino pyridine (4 gm) at 25° C. and the solution was cooled to 0-5° C. N,N-diisopropylethylamine (85 ml) was added to the solution and cooled to 0-5° C. (S)-Camphor sulfonyl chloride (100 gm) dissolved in methylenechloride (150 ml) was added slowly for 30 minutes at 5-10° C. To the reaction mass, was added acetic acid (5 ml) at 5-10° C. The pH was adjusted to 6.5-7.0 with ammonia, and then ice-cooled water (500 ml) was added and stirred for 15 minutes at 25° C. The layers were separated. The organic layer was washed with 10% aqueous sodium chloride. The organic layer was distilled under reduced pressure to obtain a residue. The residue was stirred with ethanol (744 ml) for 20 hours at 25° C. The solid obtained was collected by filtration and the solid was washed with chilled ethanol (50 ml) and diisopropylether (200 ml) to obtain a diastereomeric mixture of 1-(S)-camphor sulfonyl-5-methoxy-2-[(3,5-dimethyl-4-methoxy-2-pyridyl)methyl-(R/S)-sulfinyl]-1H-benzimidazole and 1-(S)-camphor sulfonyl-6-methoxy-2-[(3,5-dimethyl-4-methoxy-2-pyridyl)methyl-(R/S)-sulfinyl]-1H-benzimidazole (120 gm, 13:7).

The above solid (120 gm) was dissolved in tetrahydrofuran (1800 ml) at 25° C. for 30 minutes. Distilled off the solvent completely under vacuum and tetrahydrofuran (160 ml) was added. t-Butyl alcohol (160 ml) was slowly added to reaction mass for 15 minutes. Then the contents were stirred for 20 hours at 25° C. and cooled to 0-5° C. and stirred for 2 hours at 0-5° C. The solid obtained was collected by filtration and the solid was washed with chilled tetrahydrofuran and t-butyl alcohol mixture (20 ml, 1:1). Finally washed with diisopropylether (100 ml) to obtain a diastereomeric mixture of 1-(S)-camphor sulfonyl-5-methoxy-2-[(3,5-dimethyl-4-methoxy-2-pyridyl)methyl-(R/S)-sulfinyl]-1H-benzimidazole and 1-(S)-camphor sulfonyl-6-methoxy-2-[(3,5-dimethyl-4-methoxy-2-pyridyl)methyl-(R/S)-sulfinyl]-1H-benzimidazole (60 gm, 4:1).

The above solid (60 gm) was dissolved in tetrahydrofuran (900 ml) and distilled off the solvent completely under vacuum. The contents were stirred with tetrahydrofuran (90 ml) and t-butyl alcohol mixture (90 ml) for 20 hours at 25° C. Cooled to 0-5° C. and stirred for 2 hours at 0-5° C. The solid obtained was collected by filtration and the solid was washed with chilled tetrahydrofuran and t-butyl alcohol mixture (20 ml, 1:1). Finally washed with diisopropylether (100 ml) to obtain a diastereomeric mixture of 1-(S)-camphor sulfonyl-5-methoxy-2-[(3,5-dimethyl-4-methoxy-2-pyridyl)methyl-(R/S)-sulfinyl]-1H-benzimidazole and 1-(S)-camphor sulfonyl-6-methoxy-2-[(3,5-dimethyl-4-methoxy-2-pyridyl)methyl-(R/S)-sulfinyl]-1H-benzimidazole (35 gm, 9:1).

Preparative Example 2

Racemate of 5-Methoxy-2-[(3,5-dimethyl-4-methoxy-2-pyridyl)methylsulfinyl]-1H-benzimidazole (100 gm) was dissolved in dichloromethane (1000 ml) and dimethyl amino pyridine (4 gm) at 25° C. and the solution was cooled to 0-5° C. N,N-diisopropylethylamine (85 ml) was added to the solution and cooled to 0-5° C. (S)-Camphor sulfonyl chloride (100 gm) dissolved in methylenechloride (150 ml) was added slowly for 30 minutes at 5-10° C. To the reaction mass, was added acetic acid (5 ml) at 5-10° C. The pH was adjusted to 6.5-7.0 with ammonia, and then ice-cooled water (500 ml) was added and stirred for 15 minutes at 25° C. The layers were separated. The organic layer was washed with 10% aqueous sodium chloride. The organic layer was distilled under reduced pressure to obtain a residue. The residue was dissolved in tetrahydrofuran (186 ml) and added t-butyl alcohol (186 ml) slowly for 30 minutes at 25° C. The contents were stirred for 20 hours at 25° C. and cooled to 0-5° C. and stirred for 2 hours at 0-5° C. The solid obtained was collected by filtration and the solid was washed with chilled tetrahydrofuran and t-butyl alcohol mixture (30 ml, 1:1). Finally washed with diisopropylether (200 ml) to obtain a diastereomeric mixture of 1-(S)-camphor sulfonyl-5-methoxy-2-[(3,5-dimethyl-4-methoxy-2-pyridyl)methyl-(R/S)-sulfinyl]-1H-benzimidazole and 1-(S)-camphor sulfonyl-6-methoxy-2-[(3,5-dimethyl-4-methoxy-2-pyridyl)methyl-(R/S)-sulfinyl]-1H-benzimidazole (40 gm, 9:1).

Example 1

Water (580 ml) and 5% aqueous sodium chloride (70 ml) solution were added to the diastereomeric mixture of 1-(S)-camphor sulfonyl-5-methoxy-2-[(3,5-dimethyl-4-methoxy-2-pyridyl)methyl-(R/S)-sulfinyl]-1H-benzimidazole and 1-(S)-camphor sulfonyl-6-methoxy-2-[(3,5-dimethyl-4-methoxy-2-pyridyl)methyl-(R/S)-sulfinyl]-1H-benzimidazole (35 gm, 9:1) obtained as in preparative example 1 at 25° C., then sodium hydroxide solution (11 gm in 58 ml water) was added slowly for 30 minutes. The contents were stirred for 6 hours at 25° C. To the reaction mass, was added dichloromethane (350 ml), the pH was adjusted to 7.0 with hydrochloric acid and the reaction mass was extracted with dichloromethane. The layers were separated. The organic layer was washed with 5% aqueous sodium chloride (70 ml), dried with sodium sulfate and the solvent was distilled to obtain 21 gm residue containing 5-Methoxy-2-[(3,5-dimethyl-4-methoxy-2-pyridyl)methylsulfinyl]1-H-benzimidazole (esomeprazole:R-omeprazole=11:1).

Example 2

Water (660 ml) and 5% aqueous sodium chloride (80 ml) solution were added to the diastereomeric mixture of 1-(S)-camphor sulfonyl-5-methoxy-2-[(3,5-dimethyl-4-methoxy-2-pyridyl)methyl-(R/S)-sulfinyl]-1H-benzimidazole and 1-(S)-camphor sulfonyl-6-methoxy-2-[(3,5-dimethyl-4-methoxy-2-pyridyl)methyl-(R/S)-sulfinyl]-1H-benzimidazole (40 gm, 9:1) obtained as in preparative example 2 at 25° C., then sodium hydroxide solution (13 gm in 65 ml water) was added slowly for 30 minutes. The contents were stirred for 6 hours at 25° C. To the reaction mass, was added dichloromethane (400 ml), the pH was adjusted to 7.0 with hydrochloric acid and the reaction mass was extracted with dichloromethane. The layers were separated. The organic layer was washed with 5% aqueous sodium chloride (80 ml), dried with sodium sulfate and the solvent was distilled to obtain 24 gm residue containing 5-Methoxy-2-[(3,5-dimethyl-4-methoxy-2-pyridyl)methylsulfinyl]1-H-benzimidazole (esomeprazole:R-omeprazole=11:1).

Example 3

The 5-Methoxy-2-[(3,5-dimethyl-4-methoxy-2-pyridyl)methylsulfinyl]1-H-benzimidazole (40 gm, esomeprazole:R- omeprazole=11:1) obtained as in example 1 was dissolved in methanol (80 ml) at 25° C. and the solution was cooled to 10° C. Sodium hydroxide solution in methanol (10 gm in 120 ml methanol) was added slowly for 30 min. The contents were stirred for 3 hours at 5-10° C. The temperature was raised to 20-25° C. for 10 hours and then cooled to 0° C. and stirred for 2 hours at 0-5° C. The solid obtained was collected by filtration and the solid was washed with chilled methanol (20 ml) and diisopropylether (100 ml) to obtain 26 gm of sodium salt of (S)-5-Methoxy-2-[(3,5-dimethyl-4-methoxy-2-pyridyl)methylsulfinyl]1-H-benzimidazole (Esomeprazole sodium) (Enantiomeric excess: 99%).

Example 4

Sodium salt of (S)-5-Methoxy-2-[(3,5-dimethyl-4-methoxy-2-pyridyl)methylsulfinyl]1-H-benzimidazole (Esomeprazole sodium) (26 gm) obtained as in example 3 was dissolved in water (470 ml). To this solution, was added magnesium chloride solution (7.3 gm in 310 ml water), and the reaction mass was stirred 1 hour at 25° C. The solid obtained was collected by filtration and the solid was washed with water to obtain 20 gm of esomeprazole magnesium dihydrate.

We claim:
1. A process for optical purification of esomeprazole or a salt thereof, which process comprises:
   a. preparing a solution of esomeprazole sodium having 20 to 1% R-omeprazole by weight of the sum of the contents of esomeprazole and R-omeprazole in a solvent selected from an alcohol or a mixture of alcohols;
   b. precipitating esomeprazole sodium; and
   c. collecting the precipitated substantially pure esomeprazole sodium.
2. The process as claimed in claim 1, wherein the solvent used in the process is selected from methanol, ethanol and isopropyl alcohol.
3. The process as claimed in claim 2, wherein the solvent used in the process is methanol.
4. The process as claimed in claim 1, wherein the esomeprazole sodium used in step (a) has 20 to 3% of R-omeprazole by weight of the sum of the contents of esomeprazole and R-omeprazole.
5. The process as claimed in claim 4, wherein the esomeprazole sodium used in step (a) has 15 to 5% of R-omeprazole by weight of the sum of the contents of esomeprazole and R-omeprazole.

* * * * *